(12) United States Patent
Baran, Jr. et al.

(10) Patent No.: US 7,459,146 B2
(45) Date of Patent: *Dec. 2, 2008

(54) STABILIZED AEROSOL DISPERSIONS

(75) Inventors: Jimmie R. Baran, Jr., Prescott, WI (US); Brian J. Gabrio, Oakdale, MN (US); James S. Stefely, Woodbury, MN (US); Stephen W. Stein, Lino Lakes, MN (US); Thomas E. Wood, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 14 days.

This patent is subject to a terminal disclaimer.

(21) Appl. No.: 10/449,443

(22) Filed: May 30, 2003

(65) Prior Publication Data

US 2004/0241101 A1 Dec. 2, 2004

(51) Int. Cl.
*A61K 9/14* (2006.01)
*A61K 9/10* (2006.01)

(52) U.S. Cl. .................... 424/46; 424/45; 424/489; 424/490; 514/937

(58) Field of Classification Search .................... 424/45, 424/46, 489, 495, 499, 9.52, 490; 514/937
See application file for complete search history.

(56) References Cited

U.S. PATENT DOCUMENTS

| | | | |
|---|---|---|---|
| 2,801,185 A | 7/1957 | Iler | |
| 3,393,155 A | 7/1968 | Schutte et al. | |
| 4,455,205 A | 6/1984 | Olson et al. | |
| 4,478,876 A | 10/1984 | Chung | |
| 4,486,504 A | 12/1984 | Chung | |
| 4,491,508 A | 1/1985 | Olson et al. | |
| 4,522,958 A | 6/1985 | Das et al. | |
| 4,611,008 A | 9/1986 | Heinzelmann | |
| 4,680,173 A | 7/1987 | Burger | |
| 5,037,579 A | 8/1991 | Matchett | |
| 5,145,684 A * | 9/1992 | Liversidge et al. | 424/489 |
| 5,182,097 A | 1/1993 | Byron et al. | |
| 5,225,183 A | 7/1993 | Purewal et al. | |
| 5,258,225 A | 11/1993 | Katsamberis | |
| 5,262,150 A | 11/1993 | Laugier et al. | |
| 5,439,670 A | 8/1995 | Purewal et al. | |
| 5,492,688 A | 2/1996 | Byron et al. | |
| 5,508,023 A | 4/1996 | Byron et al. | |
| 5,612,021 A | 3/1997 | Mellul | |
| 5,672,662 A | 9/1997 | Harris et al. | |
| 5,676,931 A | 10/1997 | Adjei et al. | |
| 5,695,747 A | 12/1997 | Forestier et al. | |
| 5,776,434 A | 7/1998 | Purewal et al. | |
| 5,858,330 A | 1/1999 | Boltri et al. | |
| 6,001,342 A | 12/1999 | Forestier et al. | |
| 6,004,567 A | 12/1999 | Marchi-Lemann et al. | |
| 6,020,419 A | 2/2000 | Bock et al. | |
| 6,054,488 A | 4/2000 | Oliver et al. | |
| 6,245,319 B1 * | 6/2001 | Quay | 424/9.52 |
| 6,258,896 B1 | 7/2001 | Abuelyaman et al. | |
| 6,309,623 B1 * | 10/2001 | Weers et al. | 424/45 |
| 6,319,513 B1 | 11/2001 | Dobrozsi | |
| 6,467,897 B1 | 10/2002 | Wu et al. | |
| 6,586,483 B2 | 7/2003 | Kolb et al. | |
| 6,709,675 B1 | 3/2004 | Lombardin et al. | |
| 6,811,767 B1 * | 11/2004 | Bosch et al. | 424/45 |
| 6,844,429 B2 | 1/2005 | Mikata et al. | |
| 7,001,580 B2 * | 2/2006 | Baran et al. | 423/445 B |
| 7,109,247 B2 * | 9/2006 | Baran et al. | 516/31 |
| 7,129,277 B2 * | 10/2006 | Baran, Jr. | 516/22 |
| 2001/0046474 A1 | 11/2001 | Weers et al. | |
| 2002/0037316 A1 | 3/2002 | Weers et al. | |
| 2002/0128336 A1 | 9/2002 | Kolb et al. | |
| 2004/0029978 A1 | 2/2004 | Chane-Ching | |
| 2004/0081627 A1 | 4/2004 | Jinks et al. | |
| 2004/0127580 A1 | 7/2004 | Baran, Jr. | |
| 2004/0127612 A1 | 7/2004 | Baran, Jr. et al. | |
| 2004/0242730 A1 | 12/2004 | Baran, Jr. et al. | |
| 2006/0286175 A1 | 12/2006 | Baran, Jr. et al. | |
| 2007/0077209 A1 | 4/2007 | Baran, Jr. et al. | |

FOREIGN PATENT DOCUMENTS

| | | |
|---|---|---|
| CA | 2327230 | 6/2001 |
| DE | 837 243 | 4/1952 |
| EP | 0 616 525 B1 | 9/1995 |
| EP | 0 616 523 B1 | 3/1998 |
| EP | 0 616 524 B1 | 10/1998 |
| FR | 2 830 450 A1 | 4/2003 |

(Continued)

OTHER PUBLICATIONS

Alargova et al., "Stable Colloidal Dispersions of Fullerenes in Polar Organic Solvents", J. Am. Chem. Soc., 2001, vol. 123, pp. 10460-10467.

(Continued)

*Primary Examiner*—Mina Haghighatian
(74) *Attorney, Agent, or Firm*—Scott A. Bardell; Stephen F. Wolf (57) ABSTRACT

The invention relates to stabilized dispersions containing nanoparticles of use for the administration of medicaments. The dispersions comprise excipient nanoparticles, a dispersed phase comprising medicament and a continuous phase comprising propellant.

21 Claims, 3 Drawing Sheets

FOREIGN PATENT DOCUMENTS

| WO | WO 00/01371 | 1/2000 |
| WO | WO 00/06495 | 2/2000 |
| WO | WO 01/05926 | 1/2001 |
| WO | WO 02/30394 A2 | 4/2002 |
| WO | WO 02/053659 A2 | 7/2002 |

OTHER PUBLICATIONS

Kibbe Ah et al., *Handbook of Pharmaceutical Excipients*, 3rd Ed., 2000, "Colloidal Sillcon Dioxide", pp. 143-145.

* cited by examiner

STABILIZED AEROSOL DISPERSIONS

BACKGROUND

This invention relates to aerosol dispersions of use for the administration of medicaments from an aerosol.

Medicaments have been delivered from propellant-basedaerosols in a variety of forms, for example, metered dose inhalers (MDI), topical sprays and whips, with the MDI being the most common. Since the introduction of the MDI in the mid 1950s, inhalation has become the most widely used route of administration of bronchodilators and steroids locally to the airways of asthmatic patients. Compared with oral administration of bronchodilators, inhalation via an MDI offers a rapid onset of action and a low incidence of systemic side effects.

The medicinal aerosol is dependent on the propulsive force of the propellant system used in its manufacture. Traditionally, the propellant system has consisted of perfluorinated compounds, hydrofluoroalkanes (HFAs), or a mixture of chlorofluorocarbons (CFCs) which are selected to provide the desired vapor pressure and suspension stability. While such systems may be used to deliver solubilized drug, the selected bioactive agent is typically incorporated in the form of a fine particulate to provide a dispersion in the liquefied propellant. To minimize or prevent the problem of aggregation in such systems, surfactants are often used to coat the surfaces of the bioactive agent and assist in wetting the particles with the aerosol propellant. The use of surfactants in this way to maintain substantially uniform dispersions is said to "stabilize" the suspensions. In some dispersions, the use of surfactants may not be desirable. The consistent and effective delivery of a therapeutically active compound (that is, a medicament) to a living organism is generally affected by a number of parameters beyond the actual chemical identity and pharmacological activity of the medicament.

Medicinal aerosols can be an effective way to introduce a medicament into the pulmonary system via oral or nasal inhalation, but there are a number of parameters governing medicinal aerosol compositions that affect their performance. The relative importance of these parameters can vary depending on the type of dosage form used (e.g., metered dose inhaler or MDI, dry powder inhaler, nebulizer) and the type of medicament being delivered, but will usually include such things as the concentration of medicament in the dosage form, the particle size of the aerosol that is delivered to an organism, the physicochemical stability of the composition, and the ability of particles delivered to the pulmonary system to be absorbed by the body.

In order to achieve certain desirable properties or an acceptable balance of properties, it is sometimes desirable to incorporate various excipients into a medicinal aerosol composition. Many different excipients have been suggested for use in medicinal aerosols, for such things as solubilizing medicament, improving the suspension quality of medicament, increasing the emitted particle size, etc. But many proposed excipients, while providing one or more benefits, suffer from drawbacks that make them otherwise undesirable for use, such as toxicological problems, limited propellant solubility, detrimental interactions with other product components, or limited ability to be broadly utilized.

More particularly, most medicament suspensions in any of the known propellants tend to aggregate rapidly. If the particle size of the suspended material cannot be regulated and aggregation takes place, the valve orifice of the aerosol container may clog, rendering the dispensing device inoperative or, if a metering valve is employed, it may be rendered inaccurate. This unwanted aggregation or flocculation may lead to improper dosages which can lead to undesirable results, particularly in the case of highly potent, low dose medicaments. Moreover, such rapid particle aggregation also leads to fast creaming or sedimentation of the suspension. The resulting phase separation is generally addressed by vigorously shaking the MDI device immediately before use. However, patient compliance is difficult to control and many commercially available suspensions are so unstable that even slight delays between shaking and use can affect dosage uniformity.

Hence, there is an ongoing need for new and effective excipients that are useful in medicinal aerosols, particularly pressurized medicinal aerosols using hydrofluorocarbon propellants, such as HFC-134a and HFC-227. Although research investment has been made over the last decade, formulating CFC-free pressurized metered dose inhalers that are suitable in terms of the stringent functional and therapeutic requirements today continues to be of major importance.

SUMMARY

In one aspect, the invention provides a stable pharmaceutical dispersion which comprises a dispersed solid phase comprising a medicament and a continuous liquid phase comprising propellant and excipient nanoparticles.

In another aspect, the invention provides a method of treating a mammal through its respiratory tract comprising the step of administering an effective amount of a pharmaceutical dispersion according to the invention to the respiratory tract of said mammal.

In another aspect, the invention provides a metered dose inhaler which comprises an aerosol container having a metering valve, and a stable pharmaceutical dispersion of the invention disposed in the container.

In another aspect, the invention provides a method of making an aerosol dispersion comprising the steps of providing an aerosol container, and charging to said container a pharmaceutical dispersion of the invention.

In another aspect, the invention provides a method of stabilizing a pharmaceutical dispersion comprising the step of adding an effective amount of excipient nanoparticles to a dispersion which comprises a dispersed solid phase comprising a medicament and a continuous liquid phase comprising propellant.

In another aspect, the invention provides a stable pharmaceutical dispersion which consists essentially of a dispersed solid phase comprising a medicament and a continuous liquid phase comprising propellant and excipient nanoparticles.

DETAILED DESCRIPTION

The dispersions of the invention are stable dispersions that provide reproducible dosing of a medicament, in the form of an aerosol, over a useful time period without substantial agitation of the dispersion or which are easily redispersed with minimal energy input. The dispersions comprising medicament and propellant are rendered stable by incorporation of an effective amount of excipient nanoparticles into the dispersion. An "effective amount" of excipient nanoparticles is an amount that minimizes the aggregation of the medicament particles and forms stable dispersions that remain dispersed over a useful time period without substantial agitation of the dispersion or which are easily redispersed with minimal energy input. Without wishing to be bound by any theory, the nanoparticles are believed to sterically inhibit the aggregation of the dispersed phase and not through particle charge. The excipient nanoparticles used in the dispersions of the invention appear to be soluble in the continuous phase of the dispersion and do not precipitate, flocculate, etc., in the dispersions of the invention. In addition, the excipient nanoparticles do not substantially associate with the surface of the medicament particles and may be effective suspension aids at low concentrations as compared with conventional suspension aids. The stable dispersions of the invention may contain less than 0.001 weight percent of surfactant, surface-active agents, traditional emulsifiers, detergents, and/or protective colloids.

As used herein, "dispersion" means a solid distributed throughout a liquid continuous phase which does not separate over a useful time period.

As used herein, "separate" means that the solid particles in a liquid dispersion gradually settle or cream, forming distinct layers with very different concentrations of the solid particles and continuous liquid phase.

As used herein, "dispersion stability" is a description of the tendency of a dispersion to separate. For a dispersion with good dispersion stability, the particles remain approximately homogeneously distributed within the continuous phase. For a dispersion with poor dispersion stability, the particles do not remain approximately homogeneously distributed within the continuous phase and may separate.

As used herein, an "excipient" refers broadly to any inert additive other than the primary active medicament moiety used to improve some aspect of the aerosol dispersion formulation.

As used herein, "aerosol dispersion" means a medicinal dispersion which includes a medicament and propellants capable of delivering the medicament to the patient when under pressure.

As used herein, "nanoparticles" means organic or inorganic particles or molecules and combinations thereof that appear to be soluble in the continuous phase wherein each particle has nanoscale dimensions in the continuous phase and that occupies or provides a zone of steric exclusion of less than 100 nanometers, within the continuous phase.

Stabilized dispersions of the invention include surface-modified inorganic nanoparticles, surface-modified organic nanoparticles, and/or steric organic molecules having unmodified surfaces (nanoparticles). "Steric organic molecules" means single molecules (for example, polymers) that have an exclusion volume describable in nanometer diameter dimensions and comprised of covalently-bound organic units. "Steric organic molecules" do not include linear polymers that are soluble in the continuous phase. In one embodiment, they are substantially composed of the same moieties on the surface as are present in the inner portion or core of the nanoparticle. The nanoparticles are desirably individual, unassociated (i.e., non-aggregated) nanoparticles dispersed throughout the continuous phase and desirably do not irreversibly associate with each other and do not associate with the dispersed medicament. The term "associate with" or "associating with" includes, for example, covalent bonding, hydrogen bonding, electrostatic attraction, London forces, and hydrophobic interactions.

The nanoparticles are selected such that the composition formed therewith is free from a degree of particle agglomeration or aggregation that would interfere with the desired properties of the composition. The surface-modified organic or inorganic nanoparticles have surface groups that modify the "solubility" or "wettability" characteristics of the nanoparticles. The surface groups are selected to render the particle compatible with the continuous phase including, components of the continuous phase. The un-modified nanoparticles are compatible with the continuous phase without further surface modification.

One method of assessing the compatibility of the nanoparticles with the continuous phase includes determining whether the resulting composition forms a stable dispersion. Incompatible nanoparticles will not improve the quality of the suspension at expected effective concentrations. For transparent continuous phases, one useful method of assessing the compatibility of the nanoparticles with the transparent continuous phase includes the step of combining the nanoparticles and the continuous phase and observing whether the nanoparticles appear to dissolve in the continuous phase such that the resulting dispersion is transparent or translucent.

For surface-modified nanoparticles, the nature of the inorganic or organic particle component of the surface-modified nanoparticle will prevent the surface-modified particle from actually dissolving in the continuous phase, i.e., the surface-modified nanoparticles will be dispersed in the continuous phase. However, the compatibility of the surface groups with the continuous phase will give the surface-modified nanoparticles the appearance of dissolving in the continuous phase. As the size of the surface-modified nanoparticles increases, the haziness of the continuous phase generally increases. Preferred surface-modified nanoparticles are selected such that they do not settle out of the continuous phase. The further step in assessing the compatibility of the continuous phase and the surface-modified or unmodified nanoparticles includes determining whether, upon subsequent introduction of medicament particles to be dispersed in the continuous phase, the composition forms a stable dispersion.

Suitable surface groups can also be selected based upon the solubility parameter of the surface group and the continuous phase. Desirably the surface group, or the agent from which the surface group is derived, has a solubility parameter similar to the solubility parameter of the continuous phase. When the continuous phase is hydrophobic, for example, one skilled in the art can select from among various hydrophobic surface groups to achieve a surface-modified particle that is compatible with the hydrophobic continuous phase. Similarly, when the continuous phase is hydrophilic, one skilled in the art can select from hydrophilic surface groups, and, when the continuous phase is a hydrofluorocarbon, one skilled in the art can select from among various compatible surface groups. The nanoparticle can also include at least two different surface groups that combine to provide a nanoparticle having a solubility parameter that is similar to the solubility parameter of the continuous phase. The surface-modified nanoparticles are not amphiphilic.

The surface groups may be selected to provide a statistically averaged, randomly surface-modified particle.

If required, the surface groups are present on the surface of the nanoparticle in an amount sufficient to provide surface-modified nanoparticles that are capable of being subsequently dispersed in the continuous phase without aggregation. The surface groups desirably are present in an amount sufficient to form a monolayer, desirably a continuous monolayer, on the surface of the nanoparticle.

Surface modifying groups may be derived from surface modifying agents. Schematically, surface modifying agents can be represented by the formula A-B, where the A group is capable of attaching to the surface of the particle and the B group is a compatibilizing group (non-reactive with the continuous phase) or a linking group to a compatibilizing group. Compatibilizing groups can be selected to render the particle relatively more polar, relatively less polar, or relatively non-polar.

Suitable classes of surface-modifying agents include, e.g., silanes, organic acids, organic bases, alcohols, and combinations thereof.

Examples of useful silanes include organosilanes including, e.g., alkylchlorosilanes, alkoxysilanes, e.g., methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy)silane, vinyltris(isobutoxy)silane, vinyltris(isopropenoxy)silane and vinyltris(2-methoxyethoxy)silane; trialkoxyarylsilanes; isooctyltrimethoxy-silane; N-(3-triethoxysilylpropyl) methoxyethoxyethoxy ethyl carbamate; N-(3-triethoxysilylpropyl) methoxyethoxyethyl carbamate; silane functional (meth)acrylates including, e.g., 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxysilane, 3-(acryloyloxypropyl) methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy) propenyltrimethoxysilane, and 3-(methacryloyloxy)propyltrimethoxysilane; polydialkylsiloxanes including, e.g., polydimethylsiloxane, arylsilanes including, e.g., substituted and unsubstituted arylsilanes, alkylsilanes including, e.g., substituted and unsubstituted alkyl silanes including, e.g., methoxy and hydroxy substituted alkyl silanes, and combinations thereof.

Methods of surface-modifying silica using silane functional (meth)acrylates are described, e.g., in U.S. Pat. Nos. 4,491,508 and 4,455,205 (Olsen et al.); U.S. Pat. Nos. 4,478,876 and 4,486,504 (Chung); and U.S. Pat. No. 5,258,225 (Katsamberis), and incorporated herein.

Useful organic acid surface-modifying agents include, e.g., oxyacids of carbon (e.g., carboxylic acid), sulfur and phosphorus, and combinations thereof.

Representative examples of polar surface-modifying agents having carboxylic acid functionality include $CH_3O(CH_2CH_2O)_2CH_2COOH$ (hereafter MEEAA) and 2-(2-methoxyethoxy)acetic acid having the chemical structure $CH_3OCH_2CH_2OCH_2COOH$ (hereafter MEAA), acid functionalized polyethylene glycols (PEGS) such as mono(polyethylene glycol) succinate and polyethylene glycols mono substituted with acetic, propionic, or butanoic acids. Such polymers or their derivatives may be prepared as described in U.S. Pat. No. 5,672,662 or purchased commercially.

Representative examples of non-polar surface-modifying agents having carboxylic acid functionality include octanoic acid, dodecanoic acid and oleic acid.

Examples of suitable phosphorus containing acids include phosphonic acids including, e.g., octylphosphonic acid, laurylphosphonic acid, decylphosphonic acid, dodecylphosphonic acid, octadecylphosphonic acid, and phosphate or phosphonic substituted polyethylene glycols.

Useful organic base surface-modifying agents include, e.g., alkylamines including, e.g., octylamine, decylamine, dodecylamine and octadecylamine, or amine functionalized polyethylene glycols.

Examples of other useful non-silane surface modifying agents include acrylic acid, methacrylic acid, beta-carboxyethyl acrylate, mono-2-(methacryloyloxyethyl)succinate, and combinations thereof. A useful surface modifying agent that imparts both polar character and reactivity to the nanoparticles is mono(methacryloyloxypolyethyleneglycol)succinate.

Examples of suitable surface-modifying alcohols include, e.g., aliphatic alcohols including, e.g., octadecyl, dodecyl, lauryl and furfuryl alcohol, alicyclic alcohols including, e.g., cyclohexanol, and aromatic alcohols including, e.g., phenol and benzyl alcohol, polyethylene glycols, monomethyl polyethylene glycols, and combinations thereof.

A variety of methods are available for modifying the surface of nanoparticles including, e.g., adding a surface modifying agent to nanoparticles (e.g., in the form of a powder or a colloidal dispersion) and allowing the surface modifying agent to react with the nanoparticles. One skilled in the art will recognize that multiple synthetic sequences to bring the nanoparticle together with the compatibilizing group are possible and are envisioned within the scope, e.g., the reactive group/linker may be reacted with the nanoparticle followed by reaction with the compatibilizing group. Alternatively, the reactive group/linker may be reacted with the compatibilizing group followed by reaction with the nanoparticle. Other useful surface modification processes are described in, e.g., U.S. Pat. Nos. 2,801,185 and 4,522,958, and incorporated herein.

The nanoparticles are primarily inorganic or organic or a combination thereof. Examples of suitable inorganic nanoparticles include silica and metal oxide nanoparticles including zirconia, titania, ceria, alumina, iron oxide, vanadia, antimony oxide, tin oxide, alumina/silica, calcium phosphate, calcium phosphate, e.g., hydroxy-apatite, and combinations thereof, and include combined materials such as a mixture of materials or layers of materials surrounding a central inorganic or organic core. Examples of suitable organic nanoparticles include buckminsterfullerenes (fullerenes), dendrimers, propellant-insoluble sugars such as lactose, trehalose, glucose or sucrose; aminoacids, and linear or branched or hyperbranched "star" polymers such as 4, 6, or 8 armed polyethylene oxide (available from Aldrich Chemical Company, Milwaukee, Wis., or Shearwater Corporation, Huntsville, Ala.) with a variety of end groups, and combinations thereof.

Specific examples of fullerenes include $C_{60}$, $C_{70}$, $C_{82}$, and $C_{84}$. Specific examples dendrimers include polyamidoamine (PAMAM) dendrimers of Generations 2 through 10 (G2-G10) (available from Aldrich Chemical Company).

As one skilled in the art will understand, the nanoparticles described above may be used as is or surface-modified and in any combination. Insoluble nanoparticles (such as inorganics, sugars such as trehalose or lactose, or certain dendrimers) should be appropriately surface modified to make them wettable in the continuous phase. The modification may also be used to control the volume of the zone of steric exclusion. Non-limiting methods for surface modification include adsorption, ionic, or covalent chemical reaction with the "surface", or encapsulating or coating the nanoparticle with a reactive moiety to create a shell that increases the "solubility" of the particle in the continuous phase. If adsorption is the primary method of modifying the surface of the nanoparticle, the adsorbed species should be selected by one skilled in the art so as to avoid substantial desorption and subsequent modification of the surface of the medicament.

When nanoparticles are present in continuous phases containing HFAs, the nanoparticle surface may desirably be comprised of a plurality of ether, ester, or amide moieties. For continuous phases also containing cosolvents (e.g., ethanol) or dimethyl ether, propane, butane, or blends thereof, the nanoparticle surface may be more hydrophobic in nature. Desirable nanoparticle surfaces are comprised of known biocompatible materials such as polyethylene glycols, or polyesters derived from lactide or caprolactone.

PAMAM dendrimers are currently commercially available with primary amine, hydroxyl, carboxylate sodium salt, mixed amine/hydroxyl, and $C_{12}$ surface functional groups. One skilled in the art will recognize these dendrimers can be used as is or modified to make the surface compatible with the continuous phase if required.

Useful zirconia nanoparticles include zirconia nanoparticles having a combination of oleic acid and acrylic acid adsorbed onto the surface of the particle.

Useful silica nanoparticles include silica nanoparticles surface-modified with silane surface modifying agents including, e.g., acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface modifying agents including, e.g., alcohol, organosilane including, e.g., alkyltrichlorosilanes, trialkoxyarylsilanes, trialkoxy(alkyl)silanes, and combinations thereof and organotitanates and mixtures thereof.

Useful surface-modified iron oxide particles include iron oxide particles modified with long chain hydrocarbons or ethers (e.g., polyethylene glycols) derived with silyl or cyano. Useful surface-modifying groups for calcium phosphate include ionic linkages based on 1) acyl or alkyl acids such as carboxylates, phosphates or sulfates-optionally with greater than mono-valent metal cations, or 2) alkyl or amines and derivatives.

In continuous phases containing HFAs, useful surface modifiers include polyesters or esters with the above listed functionality, e.g., monofunctional PEGs having alcohol, acid, or amine functionality.

Useful surface-modifying groups for buckminsterfullerenes (fullerenes) and polyamidoamine (PAMAM) dendrimers include straight or branched alkyl groups and may range from at least $C_3$ to not greater than $C_{30}$, and may be any size or range in between $C_3$ and $C_{30}$.

The nanoparticles, whether surface-modified, or not, have an average particle diameter less than about 100 nm, in other embodiments, no greater than about 50, 40, 30, 20, 15, 10, or 5 nm, in other embodiments, from about 3 nm to about 50 nm, in other embodiments, from about 3 nm to about 20 nm, and in other embodiments, from about 5 nm to about 10 nm. If the nanoparticles are aggregated, the maximum cross sectional dimension of the aggregated particle is within any of these preferable ranges.

The nanoparticles may be in the form of a colloidal dispersion. Examples of useful commercially available unmodified silica include nano-sized colloidal silicas, available under the product designations NALCO 1040, 1050, 1060, 2326, 2327, and 2329 colloidal silica from Nalco Chemical Co., Naperville, Ill.

Useful metal oxide colloidal dispersions include colloidal zirconium oxide, suitable examples of which are described in U.S. Pat. No. 5,037,579, incorporated herein, and colloidal titanium oxide, useful examples of which are described in PCT Publication No. WO 00/06495, entitled, "Nanosize Metal Oxide Particles for Producing Transparent Metal Oxide Colloids and Ceramers," (Arney et al.), filed Jul. 30, 1998, incorporated herein.

The nanoparticles are employed in the dispersions of the invention in an effective amount to minimize aggregation of the medicament particles. Nanoparticles are generally present in an amount from 0.005 to 0.5 percent by weight and may be present in any amount or range between 0.001 and 0.5 percent by weight. In other embodiments, the dispersions of the invention contain less than 0.5, 0.4, 0.3, or 0.2 percent by weight. One skilled in the art will recognize that the effective amount required will depend upon the type of the propellant, the surface functionality and particle size of the nanoparticles, the medicament concentration and type, and the presence of other excipients. Combinations of different types of nanoparticles described herein may be used.

This invention is applicable to any medicament to be prepared as an aerosol dispersion. Non-limiting examples of other suitable medicaments include antiallergics, analgesics, bronchodilators, antihistamines, therapeutic proteins and peptides, antitussives, anginal preparations, antibiotics, antiinflammatory preparations, diuretics, hormones, or sulfonamides, such as, for example, a vasoconstrictive amine, an enzyme, an alkaloid or a steroid, and combinations of these specific examples or medicaments which may be employed are: isoproterenol, phenylephrine, phenylpropanolamine, glucagon, adrenochrome, trypsin, epinephrine, ephedrine, narcotine, codeine, atropine, heparin, morphine, dihydromorphinone, dihydromorphine, ergotamine, scopolamine, methapyrilene, cyanocobalamin, terbutaline, rimiterol, salbutamol, isoprenaline, fenoterol, oxitropium bromide, reproterol, budesonide, flunisolide, ciclesonide, formoterol, fluticasone propionate, salmeterol, procaterol, ipratropiurn, triamcinolone acetonide, tipredane, mometasone furoate, colchicine, pirbuterol, beclomethasone dipropionate, orciprenaline, fentanyl, diamorphine, and dilitiazem. Others are antibiotics, such as neomycin, cephalosporins, streptomycin, penicillin, procaine penicillin, tetracycline, chlorotetracycline and hydroxytetracycline; adrenocorticotropic hormone and adrenocortical hormones, such as cortisone, hydrocortisone, hydrocortisone acetate and prednisolone; antiallergy compounds such as cromolyn sodium, and nedocromil; protein and peptide molecules such as insulin, pentamidine, calcitonin, amiloride, interferon, LHRH analogues, IDNAase, heparin, etc. If applicable, the medicaments exemplified above may be used as either the free base or as one or more salts known to the art. Vaccines may also benefit from this approach.

The medicaments exemplified above may be used as either the free base or as one or more salts known to the art. The choice of free base or salt will be influenced by the physical stability of the medicament in the dispersion. The following salts of the medicaments mentioned above may be used: acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate (embonate), pantothenate, phosphatediphosphate, polygalacturonate, salicylate, stearate, subacetate, succinate, sulphate, tannate, tartrate, and triethiodide.

Cationic salts may also be used. Suitable cationic salts include the alkali metals, e.g., sodium and potassium, and ammonium salts and salts of amines known in the art to be pharmaceutically acceptable, e.g., glycine, ethylene diamine, choline, diethanolamine, triethanolamine, octadecylamine, diethylamine, triethylamine, 1-amino-2-propanol-amino-2-(hydroxymethyl)propane-1,3-diol and 1-(3,4-dihydroxyphenyl)-2isopropylaminoethanol.

For pharmaceutical purposes, the particle size of the medicament powder should desirably be no greater than 100 micrometers diameter, since larger particles may clog the valve or orifice of the container. In another embodiment, the particle size should be less than 25 micrometers in diameter. Desirably, the particle size of the finely-divided solid powder should for physiological reasons be less than about 25 micrometers and in another embodiment, less than about 10 micrometers in diameter. The particle size of the powder for inhalation therapy is desirably less than about 5 micrometers.

Medicinal dispersions according to the present invention contain a medicament dispersed in the dispersion in a therapeutically effective amount. "Therapeutically effective amount" means an amount sufficient to induce a therapeutic effect, such as bronchodilation or antiviral activity. The amount will vary according to factors known to those skilled in the art, such as pharmacological activity of the particular medicament, the condition being treated, the frequency of administration, the treatment site, and the presence of any other therapeutic agents being co-administered. The concentration of medicament depends upon the desired dosage, but is generally in the range of 0.01 to 15; 0.01 to 10; 0.01 to 5; 0.01 to 4; 0.01 to 3; or 0.01 to 2 percent by weight and may be present in any amount or range between 0.001 and 15 percent by weight.

Suitable propellants include, for example, a chlorofluorocarbon (CFC), such as trichlorofluoromethane (also referred to as propellant 11), dichlorodifluoromethane (also referred to as propellant 12), and 1,2-dichloro-1,1,2,2-tetrafluoroethane (also referred to as propellant 114), a hydrochlorofluorocarbon, a hydrofluorocarbon (HFC), such as 1,1,1,2-tetrafluoroethane (also referred to as propellant 134a, HFC-134a, or HFA-134a) and 1,1,1,2,3,3,3-heptafluoropropane (also referred to as propellant 227, HFC-227, or HFA-227), carbon dioxide, dimethyl ether, butane, propane, or mixtures thereof. In other embodiments, the propellant includes a chlorofluorocarbon, a hydrochlorofluorocarbon, a hydrofluorocarbon, or mixtures thereof. In other embodiments, a hydrofluorocarbon is used as the propellant. In other embodiments, HFC-227 and/or HFC-134a are used as the propellant.

Propellant is present in the dispersions of the invention in an amount of at least 70 percent by weight of the dispersion, normally from about 85 to 99.99 percent by weight.

Suitable adjuvants include alcohols such as ethyl alcohol, isopropyl alcohol, propylene glycol, hydrocarbons such as propane, butane, isobutane, pentane, isopentane, neopentane, and other propellants such as those commonly referred to as Propellants 11, 12, 114, 113, 142b, 152a 124, and dimethyl ether, and surfactants such as fluorinated and non-fluorinated surfactants, carboxylic acids, and polyethoxylates. The adjuvant should be miscible with the propellant and any co-adjuvant in the amounts employed.

The dispersions of the invention may be filled into conventional aerosol containers equipped with metering valves and dispensed in a conventional manner.

EXAMPLES

Surface-Modified Nanoparticles Preparation

Preparation of PEG-modified Silica Nanoparticles (PEG-nano $SiO_2$)

PEG-modified silica nanoparticles (PEG-nano $SiO_2$) were prepared as follows: 525 grams (g) ammonia-stabilized colloidal silica (15% solids) having an average particle size of 5 nm and a surface area of about 600 meters$^2$/gram (NALCO 2326, Nalco Chemical Co., Naperville, Ill.), was combined with 46.3 g of polyethoxylatedtrialkoxysilane (SILQUEST A1230, available from Crompton Chemicals, Middlebury, Conn.) and 203.5 g distilled water in a glass container. The container was sealed and placed into an 80° C. oven for 16 hours. The resulting precipitate composition was dried by evaporation. Toluene was added to the dried particles and the solution was refluxed with acetic anhydride to cap any unreacted —OH groups. The toluene was removed using a rotoevaporator to obtain a white powder.

Preparation of PEG-modified Iron Oxide Nanoparticles (PEG-nano $Fe_2O_3$)

Colloidal hydrolyzed iron oxide nanoparticles were prepared as follows: 1 L of 1.875 M ammonium bicarbonate solution was added dropwise with rapid stirring to 2 L of 0.375 M iron nitrate nonahydrate solution. After the addition was complete, the solution was dialyzed against deionized water by passing the deionized water slowly through a dialysis tube (roughly 1 meter in length, 1000 MWCO Spectra/Por (Spectrum Laboratories, Inc., Savannah, Ga.)) immersed in a stirred solution of the hydrolyzed ferric nitrate. After dialyzing with about 5 equivalents volume deionized water, the solution of the colloidal hydrolyzed iron oxide nanoparticles was heated to about 65° C. during the remainder of the dialysis. Dialysis was continued using an additional 7 equivalent volumes deionized water.

100 g of colloidal hydrolyzed iron oxide nanoparticles were combined with 0.71 g of 2-[2-(2-Methoxyethoxy) ethoxylacetic acid, shaken to mix, and placed into an 80° C. oven for about 18 hours. The resulting precipitate composition was dried in an oven at 150° C. to recover PEG-modified iron oxide nanoparticles (PEG -nano $Fe_2O_3$), a red-brown solid.

Preparation of Acetylated Star-PEG Organic Nanoparticles (PEG-nano Star)

Poly(ethylene oxide), (4 or 6 arm, hydroxy-terminated (Aldrich Chemical Company) was added to an excess of acetic anhydride at a temperature of 80° C. in a vessel. The mixture in the vessel was stirred under nitrogen for 24 hours followed by removal of the excess acetic anhydride under vacuum. IR analysis showed no evidence of hydroxyl groups.

Preparation of Isooctyl-substituted Silica Nanoparticles (IO-nano $SiO_2$)

Iso-octyl substituted silica nanoparticles (IO-nano $SiO_2$) were prepared as described in U.S. patent Publication No. 2002/0128336.

Preparation of PEG-modified PAMAM Dendrimers.

Surface modified PAMAM (generation 2) dendrimers (PAMAM G-2) were prepared as follows:

Synthesis of MPEG-N-Hydroxysuccinimide Ester 100 g monofunctional polyethylene glycol (Polyglykol M, 1100 MW, available from Clariant, Sulzbach am Taunus, Germany, hereinafter referred to as MPEG 1100) was azeotropically dried in toluene for 24 hours followed by the addition of 2 molar excess of sodium metal (4.2 g) with constant stirring at 50° C. The temperature was increased to 75° C. and the reaction was allowed to proceed for the next 24 hours. The reaction was cooled to room temperature, any unreacted sodium removed, and further cooled to 10° C. t-butyl bromoacetate (30 mL, 2.25 molar excess, Aldrich Chemical Company) was added and the reaction was allowed to proceed for the next 48 hours with constant stirring, with the temperature gradually increasing to room temperature. The reaction was vacuum filtered to remove the NaBr salt, and the toluene was stripped off on the rotary-evaporator. The M-PEG 1100 t-butyl ester product was dissolved in 300 mL methylene chloride and extracted with purified water (3×400 mL). The organic phase was dried with sodium sulfate, filtered, and the solvent was stripped off on the rotary-evaporator. Any residual volatiles were stripped by distillation at 110° C. under high vacuum. The product was hydrolyzed at 50° C. for 48 hours with 2.25 g of lithium hydroxide monohydrate in 175 mL of purified water. The reaction was acidified to pH 3.0 with HCl and extracted with methylene chloride (4×300 mL). The organic phase was dried with sodium sulfate, filtered, and the solvent was stripped off on the rotary-evaporator to yield 12 g of M-PEG 1100 acid which was dissolved in 150 mL tetrahydrofuran, a 2 molar excess of 2.6 g N-hydroxysuccinimide (Aldrich Chemical Company) was added, along with 2.6 g 1,3-dicyclohexylcarbodiimide (1.1 molar excess, Aldrich Chemical Company). The reaction was allowed to proceed at 0° C. for 24 hours with constant stirring. The resulting mixture was then vacuum filtered to remove the urea derived from 1,3-dicyclohexylcarbodiimide, followed by the removal of the THF on the rotary-evaporator.

Acetylated PAMAM G-2 MPEG 1100 Derivative (PAMAM G-2 MPEG 1100)

0.5 g STARBURST PAMAM G-2 (Aldrich Chemical Company) was dissolved in 100 mL N,N-dimethylformamide at 0° C., and 5.4 g MPEG 1100-N-hydroxysuccinimide ester was added. The reaction was allowed to proceed with constant stirring for 2 hours. Once warmed to room temperature, 100 mL toluene was added. The resulting solution was rinsed with purified water (5×300 mL) and 1.0 NaOH (5×200 mL). The toluene was stripped off on the rotary-evaporator, and the product was dried under high vacuum.

In order to cap off any terminal amino groups that had not reacted, the product was re-dissolved in 50 mL toluene and treated with excess acetic anhydride. Following 2 hours at 80° C., the solution was cooled slightly and 50 mL ethanol was added. All solvent was then stripped off on the rotary-evaporator, and the acetylated PAMAM G-2 MPEG 1100 derivative was dried under high vacuum.

Acetylated PAMAM G-2 MPEG 2000 Derivative (PAMAM G-2 MPEG 2000)

PAMAM G-2 MPEG 2000 derivative was prepared according to the same procedure used to make the acetylated PAMAM G-2 MPEG 1100 derivative described above except that 0.16 g STARBURST PAMAM G-2 dendrimer (Aldrich Chemical Company) and 1.5 g M-PEG 2000 succinimidyl propionate (MPEG-SPA, available from Nektar, San Carlos, Calif.) were used as the starting reagents.

Acetylated PAMAM G-4 MPEG1100 Derivative (PAMAM G-4 MPEG1100)

0.4 g STARBURST PAMAM G-4 (generation 4) dendrimer (Aldrich Chemical Company) was treated with 5.0 g MPEG1100-N-hydroxysuccinimide ester as described above for the synthesis of the acetylated PAMAM G-2 MPEG 1100 derivative. An additional 4.0 g of M-PEG-N-hydroxysuccinimide ester was added after two hours of reaction and the reaction was continued for an additional two hours in order to bring the reaction to a greater degree of completion.

Dispersion Preparation

Dispersions to be tested were prepared by weighing amounts of the excipients (if any), medicament, and ethanol into an MDI canister and then crimping a continuous valve onto the canister. A known amount of propellant was forced into the canister through the continuous valve. The canister was chilled by being placed on dry ice in order to reduce the volatility of the dispersion sufficiently so that the continuous valve could be removed from the canister and a metered valve crimped onto the canister. Each dispersion was allowed to warm and stabilize for at least twelve hours prior to testing.

Suspension Quality Shake Test

The physical stability of the MDI dispersions of Examples 1-12 and 22-29 and Comparative Examples A-D were evaluated using a suspension quality shake test. Appropriate amounts of medicament, nanoparticle dispersant, propellant, alcohol and any excipients as displayed in Tables 2 and 3 were placed in a glass vial with a polyseal cap. Each vial was shaken for 30 seconds. The vials were then left undisturbed for 20 minutes. After 20 minutes, the suspension characteristics of the vials were visually observed and recorded. The dispersions were rated according to the rating system characterized in Table 1.

TABLE 1

Visual Rating of Suspension Quality

| Visual Rating of Suspension Quality | Description of Suspension |
|---|---|
| 1 | Agglomerates formed during shaking |
| 2 | Flocculation began immediately after shaking ceased |
| 3 | Flocculation began 1-5 seconds after shaking ceased |
| 4 | Flocculation began 5-30 seconds after shaking ceased |
| 5 | Flocculation began more than 30 seconds after shaking ceased |
| 6 | No flocculation observed after 10 minutes |

Shake-Delay Medication Delivery

Shake-Delay Medication Delivery (SDMD) tests were used to evaluate the influence of delay between shaking and refilling of the metering volume on subsequent dose. To conduct SDMD tests, the MDI was primed by actuating the MDI into an exhaust hood four times, shaking the MDI just prior to each actuation. After the MDI was primed, it was shaken and held in the upright position for a specified amount of time prior to actuating one additional time into the hood. The MDI was subsequently actuated into a Unit Spray Collection Apparatus (USCA—U.S. Pharmacopeia, Section <621>, 1996). A flowrate of 30 Lpm was drawn through the USCA device. The dose emitted by the MDI was collected on the walls of the USCA or on a filter in the USCA. The amount of medicament deposited on the walls of the USCA and on the filter was determined by rinsing these components with an appropriate solvent to dissolve medicament and then subsequently analyzing the solution with an appropriate HPLC method. Tests were conducted with shake delay times of 0, 30, and 60 seconds.

Examples 1-21 and Comparative Examples A-G
MDIs Formulated with Surface-modified Inorganic Nanoparticles Formulations that included a medicament and a surface-modified inorganic nanoparticle dispersion were made up and Examples 1-12 and Comparative Examples A-D were subjected to the Suspension Quality Shake Test described above. The results of the test are shown in Table 2, below. The Comparative Examples contained no nanoparticle dispersant. The result demonstrates that the addition of small amounts of inorganic nanoparticle dispersions into MDI formulations produces formulations that stay dispersed in the in the Suspension Quality Shake Test.

TABLE 2

Shake-Delay Medication Delivery Test on MDI Formulations Stabilized With Nanoparticles

| Example | Medicament | Medicament (wt %) | Dispersant | Dispersant (wt %) | Ethanol (wt %) | HFA-134a (wt %) | Visual Ranking |
|---|---|---|---|---|---|---|---|
| 1 | pirbuterol acetate | 0.25 | PEG-nano $SiO_2$ | 0.25 | 0.0 | 99.50 | 6 |
| 2 | albuterol sulfate | 0.26 | PEG-nano star | 0.10 | 14.58 | 85.06 | 4 |
| 3 | albuterol sulfate | 0.11 | PEG-nano star | 0.21 | 9.77 | 89.91 | 6 |
| 4 | albuterol sulfate | 0.40 | PEG-nano $SiO_2$ | 0.004 | 14.44 | 85.16 | 4 |
| 5 | albuterol sulfate | 0.38 | PEG-nano $SiO_2$ | 0.039 | 14.44 | 85.15 | 4 |
| 6 | albuterol sulfate | 0.40 | PEG-nano $SiO_2$ | 0.393 | 14.46 | 84.75 | 4 |
| 7 | albuterol sulfate | 0.39 | PEG-nano $SiO_2$ | 0.004 | 5.00 | 94.60 | 4 |
| 8 | albuterol sulfate | 0.42 | PEG-nano $SiO_2$ | 0.048 | 5.53 | 94.0 | 3 |
| 9 | albuterol sulfate | 0.39 | PEG-nano $SiO_2$ | 0.442 | 5.01 | 94.15 | 3 |
| 10 | albuterol sulfate | 0.39 | PEG-nano $SiO_2$ | 0.004 | 30.01 | 69.60 | 5 |
| 11 | albuterol sulfate | 0.39 | PEG-nano $SiO_2$ | 0.037 | 29.96 | 69.61 | 5 |
| 12 | albuterol sulfate | 0.40 | PEG-nano $SiO_2$ | 0.425 | 30.06 | 69.12 | 5 |
| 13 | albuerol sulfate | 0.27 | PEG-nano $Fe_2O_3$ | 0.12 | 9.99 | 89.61 | 6 |
| 14 | albuerol sulfate | 0.25 | PEG-nano $SiO_2$ | 0.25 | 14.4 | 85.1 | |
| 15 | albuerol sulfate | 0.25 | PEG-nano $SiO_2$ | 0.10 | 14.4 | 85.3 | |
| 16 | albuerol sulfate | 0.25 | PEG-nano $SiO_2$ | 0.03 | 14.4 | 85.3 | |
| 17 | albuerol sulfate | 0.25 | PEG-nano $SiO_2$ | 0.01 | 14.4 | 85.3 | |
| 18 | albuerol sulfate | 0.25 | PEG-nano $SiO_2$ | 0.005 | 14.4 | 85.3 | |
| 19 | albuerol sulfate | 0.25 | PEG-nano $SiO_2$ | 0.001 | 14.4 | 85.3 | |
| 20[2] | [3]albuerol sulfate | 0.39 | PEG-nano $SiO_2$ | 0.25 | 14.4 | 84.9 | |
| 21 | albuerol sulfate | 0.25 | IO-nano $SiO_2$ | 0.13 | 14.4 | 85.2 | |
| Comparative Example A[1] | pirbuterol acetate | 0.25 | none | 0.0 | 4.00 | 95.5 | 2 |
| Comparative Example B | albuterol sulfate | 0.26 | none | 0.0 | 14.6 | 85.15 | 3 |
| Comparative Example C | albuterol sulfate | 0.38 | none | 0.0 | 10 | 89.6 | 3 or 4 |
| Comparative Example D | albuterol sulfate | 0.40 | none | 0.0 | 0 | 99.60 | 2 |
| Comparative Example E | albuterol sulfate | 0.25 | none | 0.0 | 14.4 | 85.4 | |
| Comparative Example F[2] | [3]albuterol sulfate | 0.39 | none | 0.0 | 14.4 | 85.2 | |
| Comparative Example G[2] | albuterol sulfate | 0.39 | none | 0.0 | 14.4 | 85.2 | |

Figure 1:
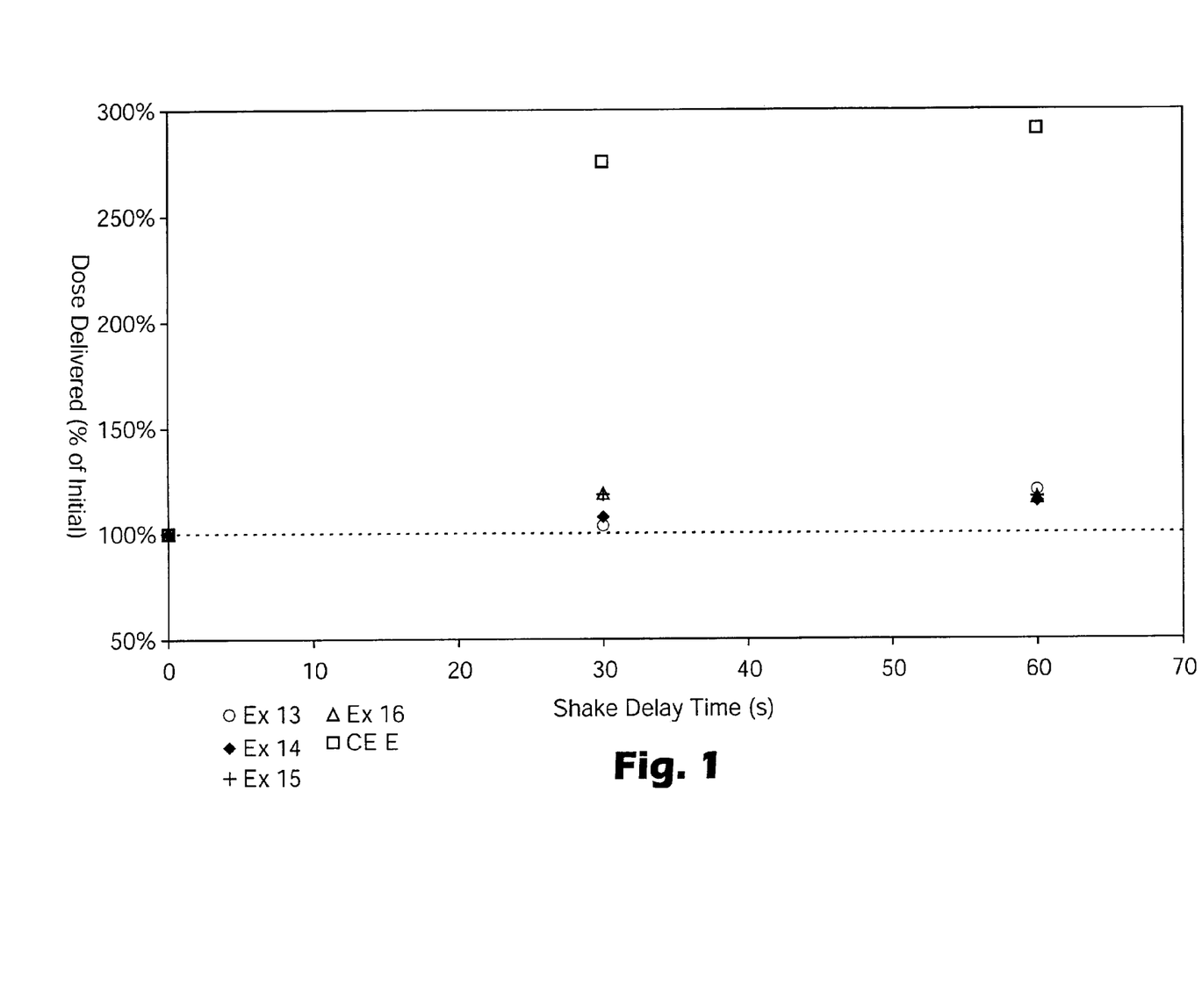
FIG. 1 shows the results of Shake-Delay Medication Delivery (SDMD) tests on Examples 13-16.
Figure 2:
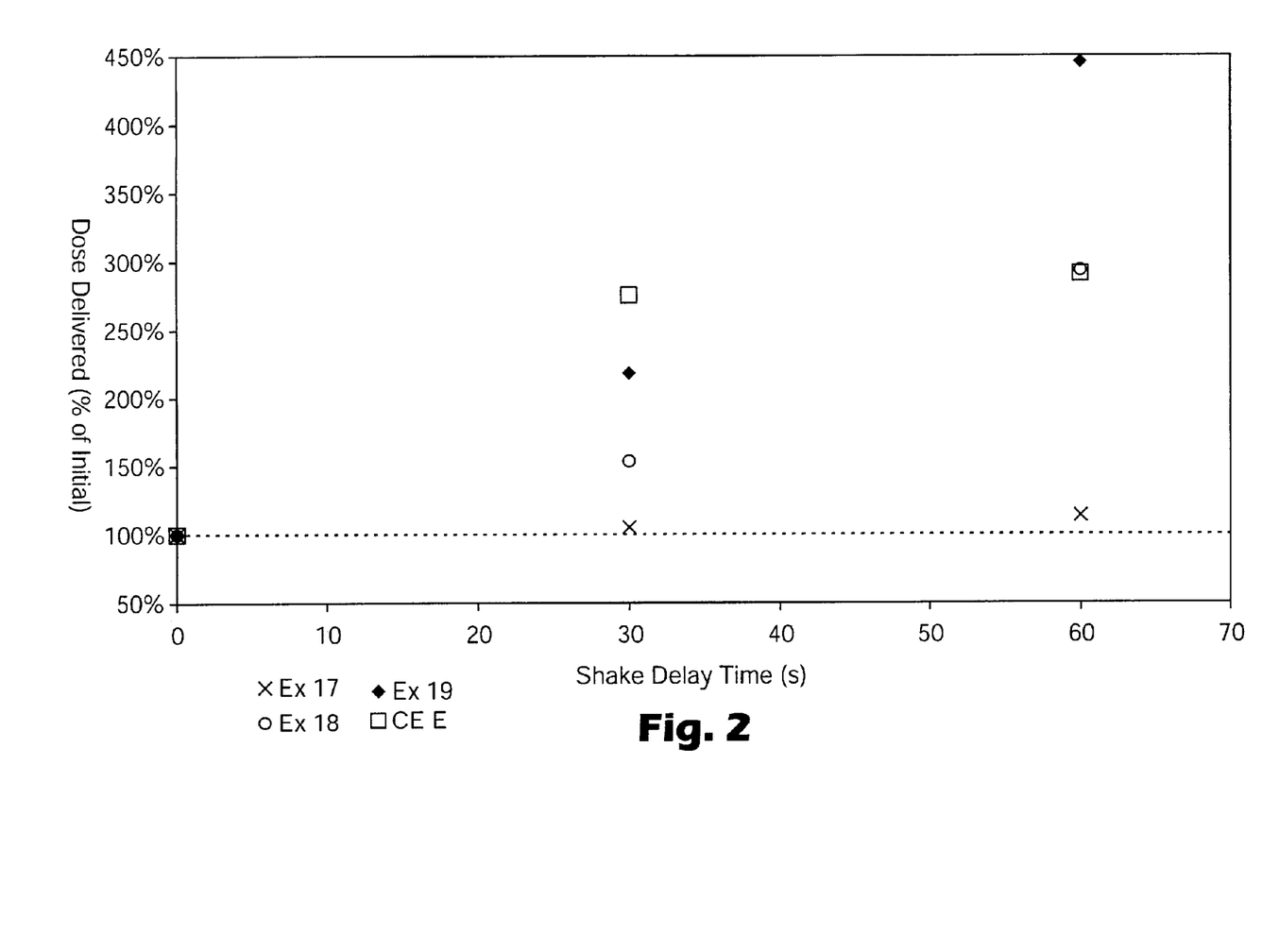
FIG. 2 shows the results of SDMD tests on Examples 17-19.
Figure 3:
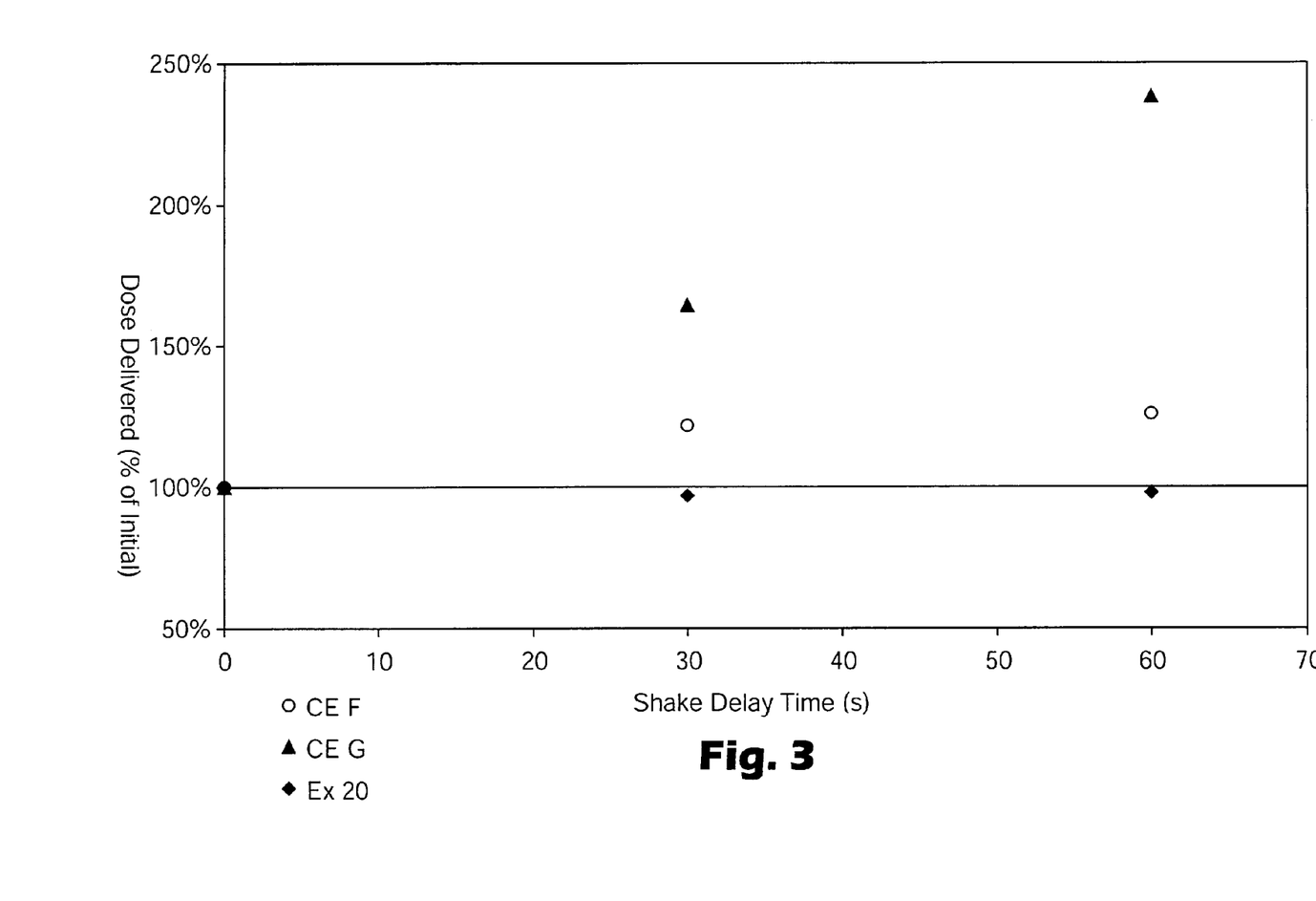
FIG. 3 shows the results of SDMD tests on Example 20.

[1] also contained 0.25 wt % oleic acid
[2] also contained 0.02 wt % oleic acid
[3] mass-median medicament particle size was 1 micrometer Examples 13-20 and Comparative Examples E, F, and G were subjected to the Shake Delay Medication Delivery Test described above. The results of those tests are shown in FIGS. 1-3. The estimated mass-median medicament particle size was 2.5 micrometers for all of the examples except where noted. FIG. 1 demonstrates that the addition of surface-modified nanoparticles (PEG-nano $Fe_2O_3$ or PEG-nano $SiO_2$) stabilized the MDI formulations containing albuterol sulfate (Examples 13-16) compared to an MDI formulation without the nanoparticle dispersant (Comparative Example E). Decreasing the amount of added nanoparticle dispersant from 0.25% to 0.03% had little effect on the stability of the formulation. FIG. 2 demonstrates that the addition of even smaller amounts of nanoparticle dispersant (0.01 to 0.001% in Examples 17-19) have an effect on stabilizing MDI formulations compared to control after 30 seconds in the Shake Delay Medication Deliver Test. FIG. 3 shows that nanoparticle dispersants are particularly effective at stabilizing MDI formulations containing medicaments with a small mass-median particle size.

Examples 22-28 MDIs Formulated with Surface-modified Organic Nanoparticles

The dispersions and visual test results for Examples 22-28 are shown in Table 3 below. For these Examples, the Comparative Examples A-D in Table 2 are the relevant comparators. The estimated mass-median medicament particle size was 2.5 micrometers for all of the examples.

TABLE 3

Shake-Delay Medication Delivery Test on MDI Formulations Stabilized With Surface-modified Organic Nanoparticles

| Example | Medicament | Medicament (wt %) | Dispersant | Dispersant (wt %) | Ethanol (wt %) | HFA-227 (wt %) | Visual Ranking |
|---|---|---|---|---|---|---|---|
| 22[1] | albuterol sulfate | 0.40 | PAMAM G-2 MPEG 1100[2] | 0.24 | 10.2 | 89.2 | 6 |
| 23[1] | albuterol sulfate | 0.39 | PAMAM G-2 MPEG 1100[2] | 0.26 | 10.08 | 89.27 | 6 |
| 24 | albuterol sulfate | 0.40 | PAMAM G-2 MPEG 1100[3] | 0.24 | 0 | 99.37 | 4 |
| 25 | albuterol sulfate | 0.39 | PAMAM G-2 MPEG 1100[3] | 0.25 | 10.07 | 89.29 | 6 |
| 26 | albuterol sulfate | 0.48 | PAMAM G-4 MPEG 1100 | 0.14 | 8.03 | 91.35 | 4 |
| 27 | albuterol sulfate | 0.46 | PEG 750 monomethyl ether bound to poly(styrene) | 0.12 | 8.88 | 90.54 | 4 |
| 28 | albuterol sulfate | 0.57 | PAMAM G-2 MPEG 2000 | 0.14 | 5.60 | 93.68 | 6 |

[1]Propellant used was HFA-134a instead of HFA-227.
[2]Before acetylation.
[3]After acetylation All patents, patent applications, and publications cited herein are each incorporated by reference, as if individually incorporated. Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A stable pharmaceutical dispersion comprising:
   a dispersed solid phase comprising a medicament; and
   a continuous liquid phase comprising propellant and excipient nanoparticles having an average particle diameter of less than 100 nm, wherein said excipient nanoparticles are present in the dispersion in an amount from 0.001 to less than 0.5 percent by weight, wherein the dispersion does not flocculate when left undisturbed for more than 30 seconds after being shaken for 30 seconds, and
   wherein the excipient nanoparticles are surface-modified and do not comprise a medicament.

2. The stable pharmaceutical dispersion according to claim 1 wherein the excipient nanoparticles are inorganic, organic, or a combination thereof.

3. The stable pharmaceutical dispersion according to claim 1 wherein the exipient nanoparticles are organic.

4. The stable pharmaceutical dispersion according to claim 1 wherein the excipient nanoparticles are selected from the group consisting of silica, zirconia, titania, ceria, alumina, vanadia, antimony oxide, tin oxide, alumina/silica, and combinations thereof.

5. The stable pharmaceutical dispersion according to claim 4 wherein the excipient nanoparticles are surface-modified with PEGs.

6. The stable pharmaceutical dispersion according to claim 3 wherein the excipient nanoparticles are selected from the group consisting of fullerenes, dendrimers, propellant-insoluble sugars, aminoacids, and combinations thereof.

7. The stable pharmaceutical dispersion according to claim 6 wherein the excipient nanoparticles are surface-modified with PEGs.

8. The stable pharmaceutical dispersion according to claim 1 wherein the excipient nanoparticles comprise branched or hyperbranched polyethylene oxide or a combination thereof.

9. The stable pharmaceutical dispersion according to claim 1 wherein the excipient nanoparticles comprise 4, 6, or 8 armed polyethylene oxide.

10. The stable pharmaceutical dispersion according to claim 1 wherein the propellant comprises a chlorofluorocarbon, a hydrochlorofluorocarbon, a hydrofluorocarbon, or mixtures thereof.

11. The stable pharmaceutical dispersion according to claim 1 wherein the propellant comprises trichlorofluoromethane; dichlorodifluoromethane; 1,2-dichloro-1,1,2,2-tetrafluoroethane; 1,1,1,2-tetrafluoroethane; 1,1,1,2,3,3,3-heptafluoropropane; carbon dioxide; dimethyl ether; butane; propane; or mixtures thereof.

12. The stable pharmaceutical dispersion according to claim 1 wherein the propellant comprises 1,1,1,2-tetrafluoroethane, 1,1,1,2,3,3,3-heptafluoropropane, or combinations thereof.

13. The stable pharmaceutical dispersion according to claim 1 wherein the medicament is selected from the group consisting of antiallergics, analgesics, bronchodilators, antihistamines, therapeutic proteins and peptides, antitussives, anginal preparations, antibiotics, anti-inflammatory preparations, adrenalcorticoptropic hormone, adrenalcortical hormones, diuretics, hormones, and sulfonamides.

14. The stable pharmaceutical dispersion according to claim 1 wherein said dispersion contain less than 0.001 weight percent surfactant.

15. The stable pharmaceutical dispersion according to claim 1 wherein said nanoparticles have an average particle diameter less than about 50 nm.

16. The stable pharmaceutical dispersion according to claim 1 wherein said nanoparticles have an average particle diameter less than about 20 nm.

17. The stable pharmaceutical dispersion according to claim 1 wherein said nanoparticles have an average particle diameter less than about 10 nm.

18. The stable pharmaceutical dispersion according to claim 1 wherein the medicament is selected from the group consisting of: isoproterenol, phenylephrine, phenylpropanolamine, glucagon, adrenochrome, trypsin, epinephrine, ephedrine, narcotine, codeine, atropine, heparin, morphine, dihydromorphinone, dihydromorphine, ergotamine, scopolamine, methapyrilene, cyanocobalamin, terbutaline, rimiterol, salbutamol, isoprenaline, fenoterol, oxitropium bromide, reproterol, budesonide, flunisolide, ciclesonide, formoterol, fluticasone propionate, salmeterol, procaterol, ipratropium, triamcinolone acetonide, tipredane, mometasone furoate, colchicine, pirbuterol, beclomethasone dipropionate, orciprenaline, fentanyl, diamorphine, dilitiazem, neomycin, cephalosporins, streptomycin, penicillin, procaine penicillin, tetracycline, chlorotetracycline, hydroxytetracycline cortisone, hydrocortisone, hydrocortisone acetate and prednisolone, cromolyn sodium, nedocromil, insulin, pentamidine, calcitonin, amiloride, interferon, LHRH analogues, lDNAase, heparin, and combinations thereof.

19. A metered dose inhaler comprising:
an aerosol container having a metering valve; and
a stable pharmaceutical dispersion of claim 1 disposed in the container.

20. A method of providing an aerosol dispersion in a container comprising the steps of:
providing an aerosol container; and
charging to said container a pharmaceutical dispersion of claim 1.

21. A method of stabilizing a pharmaceutical dispersion comprising the step of adding an effective amount of excipient nanoparticles to a dispersion comprising a dispersed solid phase comprising a medicament and a continuous liquid phase comprising propellant, wherein the dispersion does not flocculate when left undisturbed for more then 30 seconds after being shaken for 30 seconds, and wherein the excipient nanoparticles are surface-modified and do not comprise a medicament.

* * * * *